United States Patent [19]

Futhey et al.

[11] Patent Number: 5,229,797
[45] Date of Patent: Jul. 20, 1993

[54] MULTIFOCAL DIFFRACTIVE OPHTHALMIC LENSES

[75] Inventors: John A. Futhey; Michael J. Simpson, both of St. Paul, Minn.

[73] Assignee: Minnesota Mining and Manufacturing Company, Saint Paul, Minn.

[21] Appl. No.: 564,636

[22] Filed: Aug. 8, 1990

[51] Int. Cl.$^5$ .................... G02C 7/04; G02B 27/44; A61F 2/16

[52] U.S. Cl. .................... 351/161; 351/168; 359/565; 359/570; 359/571; 623/6

[58] Field of Search .............. 351/160 R, 160 H, 161, 351/162, 168; 350/452, 162.16, 162.22; 359/565, 570, 571; 623/6

[56] References Cited

U.S. PATENT DOCUMENTS

| | | | |
|---|---|---|---|
| 3,004,470 | 10/1961 | Ruhle | 350/452 |
| 4,210,391 | 7/1980 | Cohen | 351/161 |
| 4,338,005 | 7/1982 | Cohen | 351/161 |
| 4,340,283 | 7/1982 | Cohen | 351/161 |
| 4,637,697 | 1/1987 | Freeman | 351/161 |
| 4,641,934 | 2/1987 | Freeman | 351/159 |
| 4,642,112 | 2/1987 | Freeman | 623/6 |
| 4,655,565 | 4/1987 | Freeman | 351/159 |
| 4,881,804 | 11/1989 | Cohen | 351/161 |
| 4,881,805 | 11/1989 | Cohen | 351/161 |
| 4,936,666 | 6/1990 | Futhey | 350/452 |
| 4,995,714 | 2/1991 | Cohen | 351/161 |
| 5,017,000 | 5/1991 | Cohen | 351/161 |

FOREIGN PATENT DOCUMENTS

| | | |
|---|---|---|
| 3351471A2 | 1/1989 | European Pat. Off. . |
| 0335731A2 | 10/1989 | European Pat. Off. . |
| 0343067 | 11/1989 | European Pat. Off. . |
| 1235028 | 2/1967 | Fed. Rep. of Germany . |

OTHER PUBLICATIONS

Patent Abstracts of Japan, vol. 13, No. 587 (p-983) Dec. 25, 1989 & JP-A-1 250 902 (Omron Tateisi Electron Co) *abstract*.
W. N. Charman, "Diffractive Bifocal Contact Lenses," *Contax*, May 1986, pp. 11–17.
Allen L. Cohen, "An Improved Bifocal Lens Design," *Contact Lens Forum* (Nov. 1984) pp. 21–25, 28, 29, 32, and 33.
Dr. -Ing. Gunter Forst, Ber, "Examination of the Usefulness of Circular Gratings as Vision Aids," *Augen Optiker* (1966), with translation.
M. H. Freeman and J. Stone, "A New Diffractive Bifocal Contact Lens," *Transactions of the BCLA Conference*, 1987, pp. 15–22.
Hect et al., Optics (Addison-Wesley 1979), pp. 375–376.
J. A. Jordan, Jr.; P. M. Hirsch; L. B. Lesem; and D. L. Van Rooy, "Kinoform Lenses," *Applied Optics*, vol. 9, No. 8 (Aug. 1970) pp. 1883–1887.
B. Rassow and R. Kusel, "The Optics of Diffractive Intraocular Lenses," paper presented at the Fourth Congress of the German Society for Intraocular Implantation, held in Essen, Apr. 1990, with translation.
M. J. Simpson and A. G. Michette, "Imaging Properties of Modified Fresnel Zone Plates," *Optica Acta*, vol. 31, No. 4 (1984) pp. 403–413.
M. J. Simpson and A. G. Michette, "Considerations of Zone Plate Optics for Soft X-Ray Microscopy," *Optica Acta*, vol. 31, No. 12 (1984) pp. 1417–1426.
G. G. Sliusarev, "Optical Systems with Phase Layers," *Soviet Physics* —"Doklady," pp. 161–163.
Janet Stone and Anthony J. Phillops, *Contact Lenses, A Textbook for Practitioner and Student*, 2d ed. (London and Boston: Butterworths, 1981), pp. 571–591.
A. I. Tudorovskii, "An Objective with a Phase Plate," *Optika I Spektroskopiia*, vol. VI, No. 2 (Feb. 1959), pp. 126–133.
Gunter Ueberschaar, "A New Type of Bifocal Contact Lens," from Hermann Pistor Trade School for Optics, Jena Presentation made at the 16th WVA–Conference in Norderney, 1965.

*Primary Examiner*—Scott J. Sugarman
*Attorney, Agent, or Firm*—Gary L. Griswold; Walter N. Kirn; Stephen W. Buckingham

[57] ABSTRACT

A lens according to the invention has diffractive power and two primary foci, where one focus is associated with the first diffractive order and one with the second diffractive order.

12 Claims, 2 Drawing Sheets

MULTIFOCAL DIFFRACTIVE OPHTHALMIC LENSES

FIELD OF THE INVENTION

The present invention relates to ophthalmic lenses having a plurality of focal lengths.

BACKGROUND OF THE INVENTION

As used herein the term "ophthalmic lens" means vision correction lenses such as contact lenses and intraocular lenses. Other, less common, vision correction lenses such as artificial corneas and intralamellar implants are also included in this definition.

Bifocal spectacle lenses have been known for hundreds of years. In such lenses a first region of the lens is typically provided with a first focal length while a second region of the lens is provided with a second focal length. The user looks through the appropriate portion of the lens for viewing near or far objects.

More recently there has been interest in developing other types of multifocal ophthalmic lenses. Multifocal contact lenses utilizing an approach similar to that used in spectacle lenses are described in *Contact Lenses: A Textbook for Practitioner and Student*, Second Edition, Volume 2 on pages 571 through 591. Such lenses have serious drawbacks, however, because they require that the lens shift position on the eye so that different portions of the lens cover the pupil for distant and close vision. This design cannot be used for intraocular lenses or other implanted lenses, because such lenses cannot shift position. Even for contact lenses the design is disadvantageous because it is difficult to insure that the lens will shift properly on the eye for the desired range of vision.

In another design for a bifocal contact lens described in the above-referenced textbook, a central zone of the lens is provided with a first focal length and the region surrounding the central zone is provided with a second focal length. This design eliminates the necessity for shifting the lens by utilizing the phenomenon known as simultaneous vision. Simultaneous vision makes use of the fact that the light passing through the central zone will form an image of a given object at a first distance from the lens and light passing through the outer zone will form an image of the same object at a second distance from the lens. Only one of these image locations will fall on the retina and produce a properly focused image while the other image location will be either in front of or behind the retina. The improperly focused image is so defocused that it will only have the effect of reducing the contrast of the focused image. Since the sensitory response of the eye is logarithmic, a 50 to 60 percent reduction of contrast is barely perceptible and the user of such a lens receives the subjective impression of a single well-focused image.

A disadvantage of such a lens is that, if the central zone is made large enough to provide sufficient illumination in its associated image in low light situations, i.e. when the patient's pupil is dilated, the central zone will occupy all or most of the pupil area when the pupil contracts in a bright light situation. Thus bifocal operation is lost in bright light. Conversely if the central zone is made small enough to provide bifocal operation in bright light situations, an inadequate amount of the light will be directed to the image associated with the central zone in low light environments. Because the central zone is commonly used to provide distant vision, this can create a dangerous situation when the user of such a lens requires distant vision in low light situations such as when the user must drive a motor vehicle at night.

U.S. Pat. Nos. 4,637,697 and 4,642,112 (the Freeman patents) teach a different type bifocal lens in which light is directed to two different focal points by means of refraction and diffraction. A basic refractive power is supplemented by diffractive structures that split the light into a variety of diffractive orders.

A diffractive zone plate must be designed for light of a particular wavelength, $\lambda$, and will work most efficiently for light of that wavelength. According to conventional design, the radius of the $n^{th}$ zone ($r_n$) in the diffractive zone plates must be equal to $\sqrt{nr_1}$ where $r_1$ is the radius of the central zone. To a reasonable approximation $r_1$ would be equal to $\sqrt{2\lambda f}$ where $\lambda$ is the design wavelength and f is the focal length of the diffractive structure. Therefore the $n^{th}$ zone would have a radius equal to $\sqrt{2\lambda f}$.

In designing a diffractive zone plate a design wavelength, $\lambda$, must be selected. When a desired focal length and wavelength are selected, the location of the boundary of each zone, is determined. This rigid definition of the zones results in a disadvantage. If the area of the central zone is too large, under bright light situations with the pupil constricted, only a single zone or very few zones will be utilized. Thus the efficiency of the multi-focal operation is greatly reduced.

An alternative multifocal ophthalmic lens having optical power, at least a portion of the optical power being produced by diffraction, is disclosed by Simpson and Futhey in a commonly assigned U.S. patent application Ser. No., 176,701. The alternative lens also has a plurality of diffractive zones including a circular central zone and a plurality of concentric annular zones. Lenses according to this design meet the condition that $r_1^2 - r_0^2$ is not equal to $r_0^2$, where $r_0$ is the radius of the central zone and $r_1$ is the radius of the first annular zone. More specifically, $r_n$ is equal to $\sqrt{r_0^2 + 2n\lambda)f}$.

The ophthalmic lenses of the copending U.S. patent application Ser. No. 176,701, now abandoned, utilize designs for which the optical path lengths in adjacent annular zones differ by one-half of the design wavelength. These lenses direct most of the available light energy to two focal points, corresponding to the zeroth and first orders of diffraction, respectively. The zeroth order focal point is used for distant vision applications such as driving, and the first order focal point is used for near vision applications such as reading.

A property of ophthalmic zone plate lenses that utilize diffraction arises from the strong wavelength dependency inherent in the phenomenon of diffraction. Light that goes to the first diffractive order is subject to diffractive chromatic aberration and refractive chromatic aberration. Light to the zeroth order focus is subject only to refractive chromatic aberration. Refractive chromatic aberration and diffractive chromatic aberration are of opposite signs, and if equal, cancel each other out. The normal refractive chromatic aberration of the human eye is about 1 diopter. The diffractive chromatic aberration for a first order diffractive lens with 3 or 4 diopters of add power, is about $-1$ diopter, hence, for such a lens, the total chromatic aberration is essentially zero for the first order focus. Because there is no diffractive chromatic aberration for the zeroth order focus, its refractive chromatic aberration will not be canceled. Thus, such lenses can correct for chromatic aberration at one focal point, but not both.

Since the zero order of diffraction provides distant vision, while the first order of diffraction provides near vision in prior art lenses, correction of chromatic aberration for such lenses is only available for near vision. In some circumstances, for example, a patient who must drive a motor vehicle in low light conditions, chromatic aberration correction for distant vision would be more desirable.

SUMMARY OF THE INVENTION

According to the invention a lens is provided with diffractive zones including a central zone and concentric annular zones, such zones being separated from adjacent zones by optical steps having optical heights equal to $3\lambda/2$ where $\lambda$ is a design wavelength.

Alternatively phrased, the present invention is a lens having diffractive power and two foci, where one focus is associated with the first diffractive order and the second is associates with the second diffractive order.

DETAILED DESCRIPTION

Figure 1:
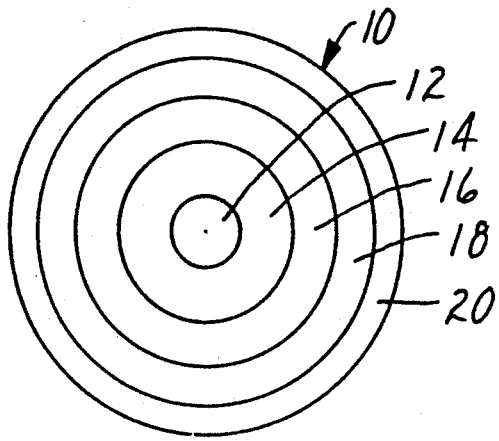
FIG. 1 is a front view of a lens having a flat surface constructed in accordance with the present invention.

An ophthalmic lens, generally designated 10 in FIG. 1, is provided with a diffractive zone plate including zones 12, 14, 16, 18, and 20. Although the drawing shows only five zones, more would typically be provided. The exact number would depend on the amount of change from the base optical power of the lens, the size of the lens and the design wavelength, among other factors. Typical lenses have between 20 and 40 zones. As will be described below the radii of the zones will be affected by several factors including the choice of a design wavelength. In preferred embodiments the design wavelength is chosen in the spectral region of the greatest photopic sensitivity of the human eye.

The lens of FIG. 1 typically has two primary optical powers provided by the combined effects of refraction and diffraction. The diffractive contributions to the two optical powers are provided by separating the zones by optical steps. An optical step causes light rays passing immediately on each side thereof to experience different optical path lengths, where the optical path length is defined in terms of wavelengths of light of a specific design wavelength. One way of providing optical steps is to provide physical structures on a surface of the lens. Alternatively optical steps may be provided on a smooth surface by varying the index of refraction of the underlying material. Such variation of the index of refraction may be accomplished, for example, by removing portions of the lens material and filling the structures formed thereby with a material having a different index of refraction or by doping portions of the lens with a dopant that causes the index of refraction of the doped regions to change.

The size of the optical steps is defined in terms of optical height. The term optical height, as used herein, refers to the difference in optical path length in terms of wavelengths of light, for adjacent light rays passing on each side of the step. Thus the optical height of a step is equal to the physical height times the difference between the refractive index of the lens and that of the surrounding medium. In the case of a lens wherein the diffractive zones are produced by modifying a portion of the lens material, the refractive index of the modified portion of the lens is substituted for that of the surrounding medium. In order to split the light between two foci, the optical height of a step should be an odd half integral multiple of the wavelength of light selected as the design wavelength. The optical height between adjacent annular zones in prior art ophthalmic multifocal lenses utilizing diffraction is one-half of the design wavelength whereas the corresponding optical height of ophthalmic lenses of the present invention is three-halves of the design wavelength.

One effect of using steps having optical heights equal to $3\lambda/2$ rather than $\lambda/2$ as in the prior art, is to shift the primary foci from the points corresponding to zeroth and first diffractive orders to those corresponding to the first and second diffractive orders. In this context a primary focus will typically receive slightly over 40 percent of the light transmitted by the lens. Thus, with two primary foci, there will remain small amounts of light scattered among a variety of foci associated with other diffractive orders. While the intensity of these other foci will not typically be high enough to permit effective vision to be associated with them, that low intensity will prevent them from interfering significantly with vision at the primary foci.

In a lens having steps with optical heights of $\lambda/2$, near vision corresponds to the first order of diffraction and distant vision corresponds to the zeroth order, whereas in a $3\lambda/2$-step lens, distant vision corresponds to the first order of diffraction and near vision corresponds to the second order of diffraction. But as taught previously, for a typical lens of 3 or 4 diopters of add power, only in the case of first order diffraction do the two kinds of chromatic aberration cancel. There is an advantage to having less aberration for the distant focus, and hence there is an advantage to a lens with optical step heights of $3\lambda/2$. An example of this is the case of an individual using this lens while driving at night where distance viewing is of primary importance.

Figure 2:
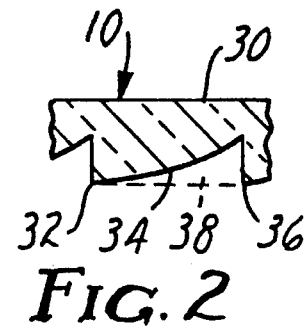
FIG. 2 is a cross-sectional view of a single zone of the lens of FIG. 1.

FIG. 2 shows a cross-sectional view of a single zone of a lens as it would be shaped on the flat surface of the lens of FIG. 1. Those skilled in the art will readily perceive that the scales in FIGS. 2 through 5 are greatly exaggerated parallel to the optical axis in order to more clearly show the nature of the structures. The anterior side 30 is smooth while the diffractive zones are provided on the posterior side. Posterior side includes diffractive zone 34 and steps 32 and 36. As previously described the optical height of step 36 is $3\lambda/2$ where $\lambda$ is the design wavelength. The diffractive zone formed by region 34 and step 36 leaves a cut out section 38 in the posterior side of the lens. As previously described, region 38 may be left open or may be filled with a material having a different index of refraction from that of the lens body. Of course, if region 38 is filled the physical height of step 36 may be required to be changed in order to maintain the desired optical height.

The shape of the zone surface will affect the diffractive orders to which energy is directed by the structure and the energy distribution among those orders. In a preferred embodiment the shape of region 34 of the illustrated zone is hyperbolic, but it is usually acceptable to use a spherical approximation, a linear approximation or even a step-wise approximation to a hyperbolic curve. The precise shape of a zone is, however, less important to the performance of the lens than the locations of the zone boundaries. The key requirement is that the zone boundaries be properly located. It is also desirable, although not strictly necessary, that the zones curve smoothly. Since a spherical zone shape is generally easier to generate than a hyperbolic shape using currently available techniques and a sphere is a reasonably close approximation to a hyperbolic surface over a small region, a spherical zone shape may be used to approximate the preferred hyperbolic contour. The spherical surfaces that are used in the preferred embodiments are designed in such a manner that the proper step height will be provided between the zones and the center of curvature of the surfaces will lie on the optical axis of the lens. Other surface shapes may also be used as long as such shapes are a good approximation to a hyperbola over the size of a zone.

It is known to provide the structured surface of a lens according to the invention with a base curve. The contour of a diffractive zone is then the algebraic sum of the base curve and the contour that the zone would have absent the base curve.

Figure 3:
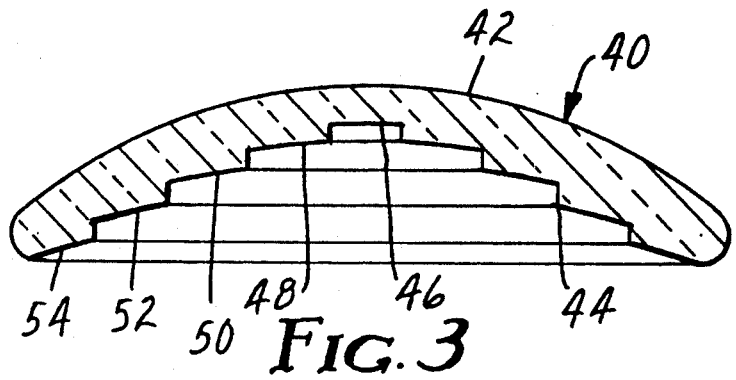
FIG. 3 is a cross-sectional view of a meniscus lens constructed in accordance with the present invention.

FIG. 3 shows a cross-sectional view through the center of such a lens, 40, utilizing a base curve. The lens is a meniscus lens having a smooth anterior side 42 and a diffractive zone plate formed by a structured posterior surface having a series of diffractive zones 46, 48, 50, 52 and 54. These zones are separated by optical steps such as step 44, separating zones 50 and 52. Alternatively the zones could be formed on the anterior side 42 of the lens, or even on both sides of the lens. The ophthalmic lenses of the invention will typically have physical steps between zones, and will typically be produced by replication techniques which are well-known in the art. As previously described the optical steps separating the diffractive zones such as optical step 44 could also be formed in other ways not requiring an actual physical step.

The center zone 46 of lens 40 has a spherical curvature defined by a radius of curvature ($R_{46}$), centered along the optical axis of lens 40. Each annular zone, 48, 50, 52 and 54, is also a segment of a spherical surface defined by a radius of curvature, $R_{48}$, $R_{50}$, $R_{52}$, and $R_{54}$, respectively, centered on the optical axis.

As stated previously, conventional techniques may be used to manufacture a lens according to the invention. For example, a lens may be injection molded using a mold that will produce the diffractive structures. Alternatively the pattern may be directly lathe cut into lens preform.

Figure 4:
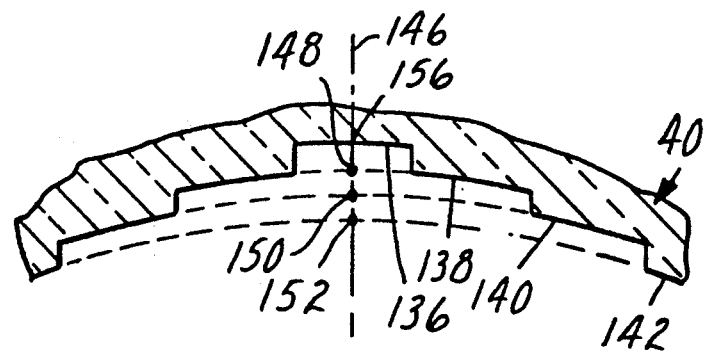
FIG. 4 is a partial cross-sectional view of diffractive zones of the lens of FIG. 3.

FIG. 4 is a partial cross-sectional view of selected annular zones of a lens such as lens 40 with the dimensions expanded along the optical axis. The lens of FIG. 4 has an optical axis, 146, and zones 136, 138, 140 and 142. The spherical surfaces corresponding to annular zones 138, 140 and 142 are extended by dashed lines to intersect optical axis 146 at points 148, 150 and 152, respectively. A set of displacement parameters $d_{138}$, $d_{140}$ and $d_{142}$, respectively, can be defined to represent the distance between intersection points 148, 150 and 152 and the intersection point 156 for the center zone 136. In selected lens design of the invention, a spherical surface, defined as a base curve, will intersect and include point 156 and the circles 158, 160 and 162 at the inner edges of annular zones. The radius of curvature of the base curve is a parameter in determining the optical powers of the multifocal diffractive lens.

The design of a lens having diffractive power according to the invention can be completely specified by the radii and height of the optical steps such as 137, 139, 141, and 143 of FIG. 4, displacement parameters $d_{138}$, $d_{140}$, $d_{142}$, and $d_{144}$, the radius of curvature $r_{136}$ of the center zone 136. Alternatively the displacements, the zone radii and the radii of curvature of the zone contours may be specified. An example ophthalmic lens design, closely related to lens 30 of FIG. 3 but including a more typical 34 zones, is described below with design parameters in Table I. The lens is an intraocular lens and the lens material is an acrylic plastic with an index of refraction of 1.492. The radius of curvature of the base curve is 22.00000 mm. Given a design wavelength of 555 nm and an index of refraction of 1.336 for the aqueous of the human eye, a physical step height of 0.00532 mm can be calculated to correspond to an optical step height of $3\lambda/2$. This step height applies for all of the optical steps of the lens. In Table I, $r_i$ is the radius of the step enclosing the $i^{th}$ zone, $R_i$ is the radius of curvature of the surface in the $i^{th}$ zone and $d_i$ is the distance between the intersection point of the base curve with the optical axis, and the intersection of the curved surface including the $i^{th}$ annular zone with the optical axis. The $0^{th}$ zone is the innermost or central zone.

TABLE I

| i | $r_i$ (mm.) | $R_i$ (mm.) | $d_i$ (mm.) |
|---|---|---|---|
| 0 | 0.39821 | 84.10114 | 0.00000 |
| 1 | 0.68972 | 84.02358 | 0.00532 |
| 2 | 0.89043 | 83.92031 | 0.01064 |
| 3 | 1.05357 | 83.81721 | 0.01596 |
| 4 | 1.19463 | 83.71428 | 0.02127 |
| 5 | 1.32071 | 83.61150 | 0.02658 |
| 6 | 1.43577 | 83.50889 | 0.03189 |
| 7 | 1.54226 | 83.40645 | 0.03720 |
| 8 | 1.64186 | 83.30416 | 0.04251 |
| 9 | 1.73576 | 83.20204 | 0.04781 |
| 10 | 1.82483 | 83.10008 | 0.05311 |
| 11 | 1.90975 | 82.99829 | 0.05841 |
| 12 | 1.99105 | 82.89665 | 0.06371 |
| 13 | 2.06916 | 82.79517 | 0.06900 |
| 14 | 2.14443 | 82.69386 | 0.07429 |
| 15 | 2.21714 | 82.59270 | 0.07958 |
| 16 | 2.28754 | 82.49170 | 0.08487 |
| 17 | 2.35584 | 82.39087 | 0.09015 |
| 18 | 2.42229 | 82.29019 | 0.09543 |
| 19 | 2.48682 | 82.18967 | 0.10071 |
| 20 | 2.54979 | 82.08931 | 0.10599 |
| 21 | 2.61124 | 81.98910 | 0.11126 |
| 22 | 2.67128 | 81.88906 | 0.11653 |
| 23 | 2.72999 | 81.78917 | 0.12180 |
| 24 | 2.78747 | 81.68944 | 0.12707 |
| 25 | 2.84379 | 81.58986 | 0.13234 |
| 26 | 2.89901 | 81.49044 | 0.13760 |
| 27 | 2.95321 | 81.39118 | 0.14286 |
| 28 | 3.00642 | 81.29207 | 0.14812 |
| 29 | 3.05871 | 81.19312 | 0.15337 |
| 30 | 3.11012 | 81.09432 | 0.15862 |
| 31 | 3.16070 | 80.99568 | 0.16387 |

TABLE I-continued

| i | $r_i$ (mm.) | $R_i$ (mm.) | $d_i$ (mm.) |
|---|---|---|---|
| 32 | 3.21047 | 80.89719 | 0.16912 |
| 33 | 3.25949 | 80.79885 | 0.17437 |

Figure 5:
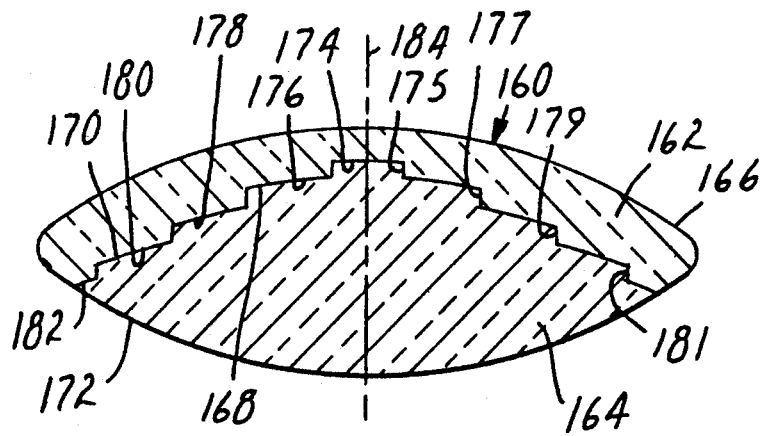
FIG. 5 is a cross-sectional view of a biconvex lens with smooth surfaces constructed in accordance with the present invention.

FIG. 5 is a view of an alternative embodiment of the invention. In FIG. 5 lens 160 is a smooth-surfaced biconvex lens comprising two lens members 162 and 164. Lens member 162 has a smooth exterior side 166, which is the anterior side of lens 160, a diffractive interior surface 168 has a circular center zone 174, and a series of annular zones 176, 178, 180 and 182. Diffractive zones 174, 176, 178, 180 and 182 are separated by circular cylindrical steps 175, 177, 179, 181 and 183, respectively, all centered about the optical axis, 184. Lens member 164 also has an interior structured surface 170, and a smooth exterior surface 172 which is the posterior surface of lens 160. The interior surface 170 is typically a replicated surface formed by casting or coating a curable liquid resin in contact with diffractive surface 168 of lens member 162, or by a separate replication or machining process. Surface 170 is bonded to, or otherwise maintained in intimate contact with, surface 168 of lens member 162. Lens members 162 and 164 have different indices of refraction, $i_{62}$ and $i_{64}$, respectively. As previously described, for lenses of the invention, the optical height of a step between adjacent annular zones is $3\lambda/2$, where $\lambda$ is the wavelength. Thus the physical step height of each step is given by:

$$(3\lambda/2)/(i_{62}-i_{64}).$$

Figure 6:
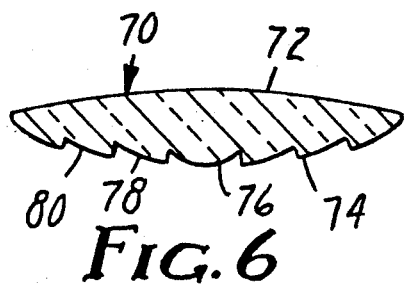
FIG. 6 is a cross-sectional view of a biconvex lens with a structured surface constructed according to the invention.

FIG. 6 shows a biconvex lens, 70, according to the invention. Unlike biconvex lens 160 of FIG. 5, lens 70 has a smooth surface 72 and a structured surface 74. Structured surface 74 has an innermost central zone 76 and annular zones such as annular zones 78 and 80.

Figure 7:
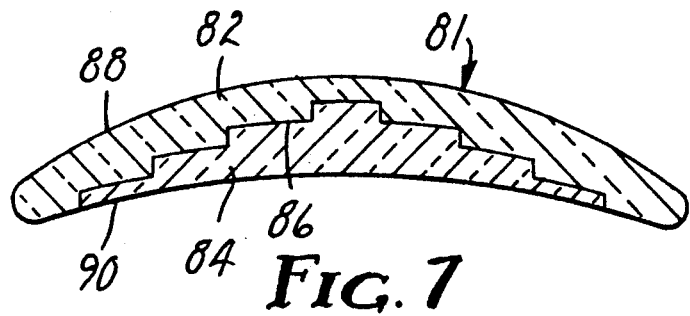
FIG. 7 is a cross-sectional view of a meniscus lens having smooth surfaces constructed according to the invention.

FIG. 7 shows a lens 81 with smooth surfaces, such as those of lens 160 of FIG. 5. Unlike lens 160, lens 81 is a meniscus lens. Lens 81 has two regions, 82 and 84, having different indices of refraction. Structured surface 86 separates regions 82 and 84, leaving smooth surfaces 88 and 90 exposed.

Figure 8:
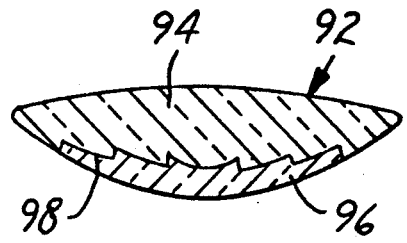
FIG. 8 is a cross-sectional view of an alternative biconvex lens with smooth surfaces constructed according to the invention.

FIG. 8 shows a smooth surfaced biconvex lens, 92, according to the invention. Lens 92 has regions 94 and 96 of materials having differing indices of refraction and separated by structured surface 98. Unlike surface 17 of lens 160 of FIG. 8, lens 92 has surface 98 with a convex underlying base curve.

It is contemplated, and clearly within the scope of the present invention, for lens designs comprising more than two lens members, or comprising two lens elements enclosing a cavity containing a vacuum or a fluid. The requirement for ophthalmic lenses of the invention is that the annular zones have a difference in optical step height between immediately adjacent zones of three-halves $\lambda$, which requires different indices of refraction on opposite sides of the diffractive surface.

We claim:

1. A multifocal ophthalmic lens having two primary optical powers both resulting from the combined effects of diffraction and refraction, said lens comprising at least one surface having a plurality of diffractive zones including a central zone and a plurality of concentric annular zones each zone separated from an adjacent zone by an optical step having an optical height substantially equal to three-halves of a design wavelength.

2. The ophthalmic lens of claim 1 wherein said design wavelength is in the spectral region of greatest photopic sensitivity of the human eye.

3. The ophthalmic lens of claim 1 wherein said lens is an intraocular lens.

4. The ophthalmic lens of claim 1 wherein said lens is a contact lens.

5. The ophthalmic lens of claim 1 wherein said lens is an artificial cornea.

6. The multifocal ophthalmic lens of claim 1 wherein said lens is an intralamellar implant.

7. The ophthalmic lens of claim 1 wherein the central zone has a radius equal to $r_0$ and the innermost annular zone has a radius equal to $r_1$ and $r_0^2$ is equal to $r_1^2 - r_0^2$.

8. The ophthalmic lens of claim 1 wherein the central zone has a radius equal to $r_0$ and the innermost annular zone has a radius equal to $r_1$ and $r_0^2$ is less than $r_1^2 - r_0^2$.

9. The ophthalmic lens of claim 1 wherein the central zone has a radius equal to $r_0$ and the innermost annular zone has a radius equal to $r_1$ and $r_0^2$ is greater than $r_1^2 - r_0^2$.

10. The ophthalmic lens of claim 1 wherein said diffractive zones are provided on a curved surface.

11. The ophthalmic lens of claim 10 wherein said curved surface is concave.

12. A lens having diffractive power and having two primary foci wherein said primary foci correspond to the positive first and second diffractive orders.

* * * * *